US012673099B2

(12) United States Patent
Hua et al.

(10) Patent No.: US 12,673,099 B2
(45) Date of Patent: Jul. 7, 2026

(54) CORONAVIRUS VACCINE BASED ON CONTROLLABLE SECRETORY EXPRESSION OF ATTENUATED SALMONELLA, PREPARATION METHOD THEREFOR, AND APPLICATION THEREOF

(71) Applicant: JIANGSU TARGET BIOMEDICAL RESEARCH INSTITUTE CO., LTD., Changzhou (CN)

(72) Inventors: Zichun Hua, Changzhou (CN); Leyang Wu, Changzhou (CN)

(73) Assignee: Jiangsu Target Biomedical Research Institute Co., Ltd., Changzhou (CN)

( * ) Notice: Subject to any disclaimer, the term of this patent is extended or adjusted under 35 U.S.C. 154(b) by 494 days.

(21) Appl. No.: 18/263,578

(22) PCT Filed: Oct. 27, 2020

(86) PCT No.: PCT/CN2020/124172
§ 371 (c)(1),
(2) Date: Jul. 31, 2023

(87) PCT Pub. No.: WO2022/087855
PCT Pub. Date: May 5, 2022

(65) Prior Publication Data
US 2024/0307523 A1 Sep. 19, 2024

(30) Foreign Application Priority Data
Oct. 26, 2020 (CN) .......................... 202011155285.8

(51) Int. Cl.
| | |
|---|---|
| *A61K 39/215* | (2006.01) |
| *A61K 39/12* | (2006.01) |
| *A61P 37/04* | (2006.01) |
| *A61K 39/00* | (2006.01) |

(52) U.S. Cl.
CPC ............ *A61K 39/215* (2013.01); *A61P 37/04* (2018.01); *A61K 2039/522* (2013.01); *A61K 2039/523* (2013.01); *A61K 2039/542* (2013.01); *A61K 2039/70* (2013.01)

(58) Field of Classification Search
CPC .................. A61K 39/12; A61K 39/215; A61K 2039/522; A61K 2039/523; A61K 2039/542; A61K 2039/70; A61P 37/04; C12N 2770/20034
See application file for complete search history.

(56) References Cited

FOREIGN PATENT DOCUMENTS

| | | |
|---|---|---|
| CN | 102335421 A | 2/2012 |
| CN | 111529701 A | 8/2020 |

OTHER PUBLICATIONS

Wu, Bao, et al. 2022; Advanced Drug Delivery Reviews, 187, 114363.*
Zhang et al., 2016. C; Oncotarget, 7 (49), 81187-81196.*
Zhang et al Cellular & Molecular Immunology, 5 (2): 91-97; 2008.*
Xu, X, Systematic Analysis of the SsrAB Virulon of *Salmonella enterica*, Infection and Immunity, Jan. 31, 2010, pp. 49-58, vol. 78, No. 1, doi:10.1128/IAI.00931-09, American Society for Microbiology.
Zhu, D., Oral delivery of SARS-CoV-2 DNA vaccines using attenuated *Salmonella typhimurium* as a carrier in rat, BioRxiv., Jul. 23, 2020, pp. 1-12, vol. 78, No. 1, doi: https://doi.org/10.1101/2020.07.23.217174.
Yang, L., Strategies for Vaccine Development of COVID-19, Chinese Journal of Biotechnology, Apr. 25, 2020, pp. 593-604, vol. 36, No., 4, DOI: 10.13345/j.cjb.200094, China Academic Journal Electronic Publishing House, english abstract only considered.
Yu, W, Biological Characteristics and Drug Development Strategy for Severe Acute Respiratory Syndrome Coronavirus 2, Chinese Journal of Pharm. Biotechnology, Feb. 29, 2020, pp. 1-7, vol. 21, No. 1, China Academic Journal Electronic Publishing House.

* cited by examiner

*Primary Examiner* — Jennifer E Graser
(74) *Attorney, Agent, or Firm* — Hudak, Shunk & Farine Co. LPA

(57) ABSTRACT

A coronavirus vaccine based on controllable secretory expression of attenuated *Salmonella*, a preparation method therefor, and use thereof. The method includes constructing controllable and stable expression plasmids for secretory expression of different antigenic structural domain proteins of the new coronaviruses and their attenuated *Salmonella* expression strains, and then mixing various attenuated *Salmonella* antigen-presenting strains that can achieve controllable intracellular secretory expression in antigen-presenting cells. With the aid of a unique secretion system, a variety of different antigenic proteins can be secretory-expressed efficiently in antigen-presenting cells after oral gavaging. The secretory-expressed antigenic proteins can be efficiently processed and presented by the antigen-presenting cells, and finally activate/regulate the immune system to produce more potent antibodies to make the vaccine work.

10 Claims, 4 Drawing Sheets

Specification includes a Sequence Listing.

SEQUENCE LISTING

```
<160> NUMBER OF SEQ ID NOS: 28

<210> SEQ ID NO 1
<211> LENGTH: 385
<212> TYPE: DNA
<213> ORGANISM: Artificial Sequence (NirB Promoter)
<220> FEATURE:
<223> OTHER INFORMATION: synthesized

<400> SEQUENCE: 1
gagggttacc ggcccgatcg ttgaacatag cggtccgcag gcggcactgc ttacagcaaa      60
cggtctgtac gctgtcgtct ttgtgatgtg cttcctgtta ggtttcgtca gccgtcaccg     120
tcagcataac accctgacct ctcattaatt gctcatgccg gacggcacta tcgtcgtccg     180
gccttttcct ctcttccccc gctacgtgca tctatttcta taaacccgct cattttgtct     240
attttttgca caaacatgaa atatcagaca attccgtgac ttaagaaaat ttatacaaat     300
```

-continued

```
cagcaatata cccattaagg agtatataaa ggtgaatttg atttacatca ataagcgggg    360
ttgctgaatc gttaaggtag gcggt                                          385

<210> SEQ ID NO 2
<211> LENGTH: 397
<212> TYPE: DNA
<213> ORGANISM: Artificial Sequence (SseA Promoter)
<220> FEATURE:
<223> OTHER INFORMATION: synthesized

<400> SEQUENCE: 2
agaagagaac aacggcaagt tacaggatcc gcagcaatat cagcaaaaca ccttattgct     60
tgaagcgatc gagcaggccg aaaatatcat caacattatt tattatcgtt accataacag    120
cgcacttgta gtgagtgagc aagagtaaag taaaaatatc ttagagccta tcccaccagg    180
cgttaattgg cgcagccagt ttggacacgg atagcgcgca aaaaccgcag cgtacacgta    240
gtacgtgagg tttgactcgc tacgctcgcc cttcgggccg ccgctagcgg cgttcaaaac    300
gctaacgcgt tttggcgagc actgcccagg ttcaaaatgg caagtaaaat agccctaatg    360
ggataggctc ttagttagca cgttaattat ctatcgt                            397

<210> SEQ ID NO 3
<211> LENGTH: 374
<212> TYPE: DNA
<213> ORGANISM: Artificial Sequence (SseJ Promoter)
<220> FEATURE:
<223> OTHER INFORMATION: synthesized

<400> SEQUENCE: 3
tcacataaaa cactagcact ttagcaataa tagtcggatg ataagtttgt ctgttttttcc    60 tgagtatcaa gccagctcat actcacgcca gcacactaaa atcaggagtg gcttcttttt    120
tagatctttg ccttagccag gcgcacactc aataatgata gcagtcagat aatatgtacc    180
aggcattaac ctcacgttgt tgatgatata tttacttcgt tgaaaaacaa taaacattgt    240
atgtatttta ttggcgacga aaaactgtta aagaagcgta attccatata caccatttac    300
ctgattactt ttcttgctaa tatttgctaa ttaattattt gctaaagcgt gtttaataaa    360
gtaaggagga cact                                                     374

<210> SEQ ID NO 4
<211> LENGTH: 388
<212> TYPE: DNA
<213> ORGANISM: Artificial Sequence (SifB Promoter)
<220> FEATURE:
<223> OTHER INFORMATION: synthesized

<400> SEQUENCE: 4
ctgccctacc gctaaacatc tcattgttgt tagcctaata atacttttag tttaacttct     60
tataagacaa tttctacacg gttgagcaac tatttacttt ctctaaaaat aatatagtgc    120
gtaattaatc attactcata gtacatgatg atgtgagaat taagaaaacc gttttacttt    180
cattcgtttt atctgacata tttcatggcc aggaggcgtg ggcatgacta aagctacggg    240
tcgatttgaa caattgaaca ataatgttga cggttcagga caaagcaaaa atcaggtgtt    300
tcaccgatag gcaaaccgat gggcaacatg ggataatatt tcgaatacca cctattccag    360
taatgaagta tcatataatc acttgtgg                                      388

<210> SEQ ID NO 5
<211> LENGTH: 1224
```

```
<212> TYPE: DNA
<213> ORGANISM: Artificial Sequence (SseJ Signal Peptide)
<220> FEATURE:
<223> OTHER INFORMATION: synthesized

<400> SEQUENCE: 5
atgccattga gtgttggaca gggttatttc acatcatcta tcagttctga aaaatttaat      60
gcgataaaag aaagcgcacg ccttccggaa ttaagtttat gggagaaaat caaagcatat     120
ttctttacca cccaccatgc agaggcgctc gaatgtatct ttaatcttta ccaccatcag     180
gaactgaatc taacaccggt acaggttcgc ggagcctaca tcaaacttcg agccttagcg     240
tctcagggat gtaaagaaca gtttattata gaatcacagg aacacgccga taagttgatt     300
attaaagatg ataatggtga aaatattttg tctattgagg ttgaatgtca tccggaagct     360
tttggtcttg caaagaaat caataaatca catcccaagc ccaaaaatat ttctttgggt      420
gatattacca gactggtatt ttttggcgac agcttgtctg actccttagg gcgtatgttt     480
gaaaaaacac atcatatctt accctcctat ggtcaatact ttggcggaag gtttactaat     540
ggatttacct ggactgagtt tttatcatct ccacacttct taggtaaaga gatgcttaat     600
tttgctgaag gggaagtac atcggcaagc tattcctgct ttaattgcat cggtgacttt      660
gtatcaaata cggacagaca agtcgcatct tacacccctt ctcaccagga cctggcgata     720
tttttattgg gggctaatga ctatatgaca ctacacaaag ataatgtaat aatggtcgtt     780
gagcaacaaa ttgatgatat tgaaaaaata atttccggtg gagttaataa tgttctggtc     840
atggggattc ccgatttgtc tttaacacct tatggcaaac attctgatga aaaaagaaag     900
cttaaggatg aaagcatcgc tcacaatgcc ctgttaaaaa ctaatgttga agaattaaaa     960
gaaaaatacc cccagcataa aatatgctat tacgagactg ccgatgcatt taaggtgata    1020
atggaggcgg ccagtaatat tggttatgat acggaaaacc cttatactca ccacggctat    1080
gtacatgttc ccgggggctaa agaccctcag ctagatatat gtccgcaata cgtcttcaac    1140
gaccttgtcc atccaacccca ggaagtccat cattgttttg ccataatgtt agaaagtttt    1200
atagctcatc attattccac tgaa                                           1224

<210> SEQ ID NO 6
<211> LENGTH: 576
<212> TYPE: DNA
<213> ORGANISM: Artificial Sequence (RBD)
<220> FEATURE:
<223> OTHER INFORMATION: synthesized

<400> SEQUENCE: 6
ccgaacatca ccaacctgtg cccgtttggc gaggttttca acgcgacccg tttcgcgagc      60
gtgtatgcgt ggaaccgtaa acgtatcagc aactgcgttg cggactatag cgtgctgtac     120
aacagcgcga gcttcagcac ctttaagtgc tatggtgtga gcccgaccaa actgaacgat     180
ctgtgcttta ccaacgttta cgcggatagc ttcgtgattc gtggcgacga ggttcgtcag     240
atcgcgccgg gtcaaaccgg caagattgcg gactacaact ataaactgcc ggacgatttc     300
accggctgcg ttatcgcgtg gaacagcaac aacctggata gcaaagtggg tggcaactac     360
aactatctgt accgtctgtt tcgtaagagc aacctgaaac gttcgagcg tgacattagc      420 accgaaatct accaggcggg tagcacccccg tgcaacggtg ttgagggctt taactgctat     480
ttcccgctgc aaagctacgg tttccaaccg accaacggtg ttggttacca gccgtaccgt     540
gtggttgtgc tgagctttga actgctgcac gcgccg                               576
```

<210> SEQ ID NO 7
<211> LENGTH: 870
<212> TYPE: DNA
<213> ORGANISM: Artificial Sequence (NTD)
<220> FEATURE:
<223> OTHER INFORMATION: synthesized

<400> SEQUENCE: 7
gtgaatctga ccacccgcac ccaactgccg ccggcgtaca ccaacagctt cacccgtggt        60
gtttactatc cggacaaagt ttttcgtagc agcgtgctgc acagcaccca ggacctgttc       120
ctgccgttct ttagcaacgt tacctggttc cacgcgatcc acgtgagcgg caccaacggc       180
accaagcgtt tcgacaaccc ggtgctgccg tttaacgatg gtgtttactt cgcgagcacc       240
gagaagagca acatcattcg tggttggatt tttggcacca ccctggacag caaaacccag       300
agcctgctga tcgttaacaa cgcgaccaac gtggttatta aggtgtgcga gttccaattt       360
tgcaacgatc cgttcctggg cgtttactat cacaagaaca acaaaagctg gatggagagc       420
gaatttcgtg tttatagcag cgcgaacaac tgcacctttg agtacgtgag ccagccgttc       480
ctgatggacc tggaaggcaa gcaaggcaac ttcaaaaacc tgcgtgagtt cgtgttcaag       540
aacattgatg gttacttcaa aatctacagc aagcacaccc cgatcaacct ggttcgtgac       600
ctgccgcagg gttttagcgc gctggagccg ctggttgacc tgccgatcgg tattaacatc       660
acccgttttc aaaccctgct ggcgctgcac cgtagctacc tgacgccggg tgacagcagc       720
agcggttgga ccgctggtgc tgcggcgtac tatgttggtt acctgcaacc gcgtaccttc       780
ctgctgaaat acaacgaaaa cggcaccatc accgatgcgg ttgattgcgc gctggacccg       840
ctgagcgaaa ccaagtgcac cctgaagagc                                       870

<210> SEQ ID NO 8
<211> LENGTH: 576
<212> TYPE: DNA
<213> ORGANISM: Artificial Sequence (S2)
<220> FEATURE:
<223> OTHER INFORMATION: synthesized

<400> SEQUENCE: 8
ggtgcgggtg cggcgctgca atcccgttt gcgatgcaaa tggcgtatcg tttcaacggt        60
attggcgtta cccagaacgt gctgtacgag aaccagaagc tgatcgcgaa ccaatttaac       120
agcgcgattg gtaaaatcca ggatagcctg agcagcaccg cgagcgcgct gggcaaactg       180
caagatgttg tgaaccagaa cgcgcaagcg ctgaacaccc tggttaagca gctgagcagc       240
aacttcggtg cgattagcag cgtgctgaac gacatcctga gccgtctgga caaagttgag       300
gcggaagtgc aaattgaccg tctgatcacc ggccgtctgc aaagcctgca aacctatgtg       360
acccagcaac tgattcgtgc ggcggaaatt cgtgcgagcg cgaacctggc ggcgaccaag       420
atgagcgagt gcgttctggg tcagagcaag cgtgtggact tttgcggtaa aggctatcac       480
ctgatgagct ccccgcagag cgcgccgcac ggcgttgtgt ttctgcacgt tacctacgtg       540
ccggcgcaag aaaagaactt taccaccgcg ccggcg                                576

<210> SEQ ID NO 9
<211> LENGTH: 45
<212> TYPE: DNA
<213> ORGANISM: Artificial Sequence (Linker)
<220> FEATURE:
<223> OTHER INFORMATION: synthesized

<400> SEQUENCE: 9

-continued

```
ggcggagggg gtagcggtgg tggcggcagc ggaggtggag gcagc                45

<210> SEQ ID NO 10
<211> LENGTH: 1997
<212> TYPE: DNA
<213> ORGANISM: Artificial Sequence (AT)
<220> FEATURE:
<223> OTHER INFORMATION: synthesized

<400> SEQUENCE: 10
gcccggggga tccgatactc tctcctttca tcgaaataac cctatgaaaa atatggctgc       60
aatcatcttg aatagtagac tcacaagggc taatacaaag cgccaaaaga ccaaacaaaa      120
taccagtatt gccaaaaata ctacgaagtt taaatgcaca gctgcagcat ggcgcataag      180
tatttcgcca acaaatagga ctgacaatag aggaatgatt ttattcatat ggatctcctt      240
ctttctctta ggttatcggg tgttgcccgc ttatttcgca ccacctaagc ggcgggggcg      300
gttggagcga ttggtgcgaa ataagaacca ttcccttagt tactaggttt tttgtcctta      360
tttcacacat tctcactttt cggtataaat gattattgcc tttttcctc tcaaatcgtt       420 gatatggcat tcgtttacgg tcaagttcag gatccataag cgactaatgc caattgcaat      480
aggaaataaa cggttacccg ttacgttgga tgaaaagaga caaaaagaat tgcagcaact      540
aaagcagaag tacggcaaaa gtgaatccag gattatgtgt attgcgttag atttattgat      600
tgcccaagaa aaagcaggat ttgaggtacc agcactcaaa aagtgacgtc acctttttatc     660 ctaaaaacta aaagtgatag cacttttaat tataagaagt tagaatatta atcatttgct      720
taattgtaca atataatgta caattgtttt atagaaataa ataaggggtg aaaggaatgg      780
aagcagtagc ttattcaaat ttccgccaaa atttacgtag ttatatgaaa caagttaatg      840
aggatgctga aacacttatt gtaacaagta aagatgtaga agatacagtt gttgtattat      900
caaaaagaga ttatgattct atgcaagaaa cgttgagaac actttctaat aattacgtca      960
tggaaaaaat tcgtcgagga gatgaacaat tctccaaagg tgcatttaaa acacatgact     1020
taatcgaggt tgaatctgat gattaaggct tggtctgatg atgcttggga tgattatctt     1080
tattggcatg agcaaggaaa caaaagcaat ataaaaaaga ttaacaagtt aataaaagat     1140
atcgatcgtt ccccctttgc tggattagga aaacctgagc cattaaagca tgatttatct    1200
ggaaaatggt ccagaagaat tacagatgaa catagactga tatatagagt tgaaaatgaa     1260
acgatattta tttattctgc aaaagatcac tattaaccaa tcggaagtaa ggaaagggtc     1320
agaaacttaa aagtttttga tccttatttt atttaccta gtcatttaaa aagctaatat      1380
agcttagtgt tgattgttat taatgaatgt gtttgttacg cgtattacgg atataaggtt     1440
agtaaaatca tttctaaagt tgaggaaaag taaatataaa tggcttaaat ttcaacaatt     1500
tgaagttgaa tagatatgtt ataatactat tgtagtgtgg gatgttagtt actaaaggat     1560
gacgcttata tatatgactg aatagaataa gcaataggtt taataatcta ttttaaattt     1620
tttgtactag ttttagtcaa ttagcaaaaa caacaaaaat aaacttctca tagaatttag     1680
ctaaaaatta atgatttatt tacatattaa atttggatac agttaagtaa tttttatata     1740
ttggaggaga agtaatggaa tataaattta acttgaattt gaaagaagta tcgagctcgg     1800
aagcttggca gcggccgctg gcgggtgtgt cgagtggatg gtaggatcga caaagatctg     1860
gctacactcg atcagcagtt agataataaa atcgctatcc atcgaagatg gatgtgtgtt     1920
ggttttttgt gtgtgtaacg caacgattga tagcataacc ccttggggcc tctaaacggg     1980
```

-continued

```
tcttgaggggg tttttttg                                                          1997

<210> SEQ ID NO 11
<211> LENGTH: 40
<212> TYPE: DNA
<213> ORGANISM: Artificial Sequence (PNirB P1 Primer)
<220> FEATURE:
<223> OTHER INFORMATION: synthesized

<400> SEQUENCE: 11
gcaaaatccc ttataagaat tgagggttac cggcccgatc                                   40

<210> SEQ ID NO 12
<211> LENGTH: 40
<212> TYPE: DNA
<213> ORGANISM: Artificial Sequence (PNirB P2 Primer)
<220> FEATURE:
<223> OTHER INFORMATION: synthesized

<400> SEQUENCE: 12
cctctttctc tagtatctag accgcctacc ttaacgattc                                   40

<210> SEQ ID NO 13
<211> LENGTH: 40
<212> TYPE: DNA
<213> ORGANISM: Artificial Sequence (PSseA P1)
<220> FEATURE:
<223> OTHER INFORMATION: synthesized

<400> SEQUENCE: 13
caaaatccct tataagaatt agaagagaac aacggcaagt                                   40

<210> SEQ ID NO 14
<211> LENGTH: 40
<212> TYPE: DNA
<213> ORGANISM: Artificial Sequence (PSseA P2 Primer)
<220> FEATURE:
<223> OTHER INFORMATION: synthesized

<400> SEQUENCE: 14
tgtccaacac tcaatggcat acgatagata attaacgtgc                                   40

<210> SEQ ID NO 15
<211> LENGTH: 40
<212> TYPE: DNA
<213> ORGANISM: Artificial Sequence (PsifB P1 Primer)
<220> FEATURE:
<223> OTHER INFORMATION: synthesized

<400> SEQUENCE: 15
caaaatccct tataagaatt ctgccctacc gctaaacatc                                   40

<210> SEQ ID NO 16
<211> LENGTH: 40
<212> TYPE: DNA
<213> ORGANISM: Artificial Sequence (PsifB P2 Primer)
<220> FEATURE:
<223> OTHER INFORMATION: synthesized

<400> SEQUENCE: 16
tgtccaacac tcaatggcat ccacaagtga ttatatgata                                   40

<210> SEQ ID NO 17
<211> LENGTH: 40
<212> TYPE: DNA
<213> ORGANISM: Artificial Sequence (sseJ P1 Primer)
```

```
<220> FEATURE:
<223> OTHER INFORMATION: synthesized

<400> SEQUENCE: 17
tatcatataa tcacttgtgg atgccattga gtgttggaca                    40

<210> SEQ ID NO 18
<211> LENGTH: 40
<212> TYPE: DNA
<213> ORGANISM: Artificial Sequence (sseJ P2)
<220> FEATURE:
<223> OTHER INFORMATION: synthesized

<400> SEQUENCE: 18
gccttcagtg gaataatgat gagctataaa actttctaac                    40

<210> SEQ ID NO 19
<211> LENGTH: 40
<212> TYPE: DNA
<213> ORGANISM: Artificial Sequence (PsseJ-sseJ P1 Primer)
<220> FEATURE:
<223> OTHER INFORMATION: synthesized

<400> SEQUENCE: 19
caaaatccct tataagaatt tcacataaaa cactagcact                    40

<210> SEQ ID NO 20
<211> LENGTH: 40
<212> TYPE: DNA
<213> ORGANISM: Artificial Sequence (PsseJ-sseJ P2 Primer)
<220> FEATURE:
<223> OTHER INFORMATION: synthesized

<400> SEQUENCE: 20
gccttcagtg gaataatgat gagctataaa actttctaac                    40

<210> SEQ ID NO 21
<211> LENGTH: 36
<212> TYPE: DNA
<213> ORGANISM: Artificial Sequence (RBD P1 Primer)
<220> FEATURE:
<223> OTHER INFORMATION: synthesized

<400> SEQUENCE: 21
agcggaggtg gaggcagccc gaacatcacc aacctg                        36

<210> SEQ ID NO 22
<211> LENGTH: 38
<212> TYPE: DNA
<213> ORGANISM: Artificial Sequence (RBD P2 Primer)
<220> FEATURE:
<223> OTHER INFORMATION: synthesized

<400> SEQUENCE: 22
tctggaacat cgtatgggta cggcgcgtgc agcagttc                      38

<210> SEQ ID NO 23
<211> LENGTH: 38
<212> TYPE: DNA
<213> ORGANISM: Artificial Sequence (NTD P1 Primer)
<220> FEATURE:
<223> OTHER INFORMATION: synthesized

<400> SEQUENCE: 23
gcagcggagg tggaggcagc gtgaatctga ccacccgc                      38
```

-continued

```
<210> SEQ ID NO 24
<211> LENGTH: 39
<212> TYPE: DNA
<213> ORGANISM: Artificial Sequence (NTD P2 Primer)
<220> FEATURE:
<223> OTHER INFORMATION: synthesized

<400> SEQUENCE: 24
tctggaacat cgtatgggta gctcttcagg gtgcacttg                              39

<210> SEQ ID NO 25
<211> LENGTH: 36
<212> TYPE: DNA
<213> ORGANISM: Artificial Sequence (S2 P1 Primer)
<220> FEATURE:
<223> OTHER INFORMATION: synthesized

<400> SEQUENCE: 25
agcggaggtg gaggcagcgg tgcgggtgcg gcgctg                                 36

<210> SEQ ID NO 26
<211> LENGTH: 40
<212> TYPE: DNA
<213> ORGANISM: Artificial Sequence (S2 P2 Primer)
<220> FEATURE:
<223> OTHER INFORMATION: synthesized

<400> SEQUENCE: 26
tctggaacat cgtatgggta cgccggcgcg gtggtaaagt                             40

<210> SEQ ID NO 27
<211> LENGTH: 25
<212> TYPE: DNA
<213> ORGANISM: Artificial Sequence (Vec P1 Primer)
<220> FEATURE:
<223> OTHER INFORMATION: synthesized

<400> SEQUENCE: 27
tacccatacg atgttccaga ttacg                                            25

<210> SEQ ID NO 28
<211> LENGTH: 20
<212> TYPE: DNA
<213> ORGANISM: Artificial Sequence (Vec P2 Primer)
<220> FEATURE:
<223> OTHER INFORMATION: synthesized

<400> SEQUENCE: 28
gctgcctcca cctccgctgc                                                  20
```

CORONAVIRUS VACCINE BASED ON CONTROLLABLE SECRETORY EXPRESSION OF ATTENUATED SALMONELLA, PREPARATION METHOD THEREFOR, AND APPLICATION THEREOF

INCORPORATED BY REFERENCE

The instant application contains a Sequence Listing which has been submitted electronically in ASCII format and is hereby incorporated by reference in its entirety. Said ASCII copy is named SequenceListingPCTCN2020124172.txt and is 13 kilobytes in size.

FIELD OF THE INVENTION

The present invention relates to the field of biotechnology, specifically to a new coronavirus vaccine based on controllable secretory expression of attenuated *Salmonella*, the preparation method therefor, and uses thereof.

BACKGROUND OF THE INVENTION

The 2019 coronavirus (COVID-19) pandemic caused by severe acute respiratory syndrome coronavirus 2 (SARS-CoV-2) is the most severe challenge to humanity in a century, cumulatively infecting more than 27 million people and causing more than 800,000 deaths as of Sep. 1, 2020. The new coronavirus shares approximately 82% genomic similarity with SARS coronavirus (SARS-CoV) from the 2003 outbreak, and both coronaviruses also share the same cellular receptor, i.e., angiotensin-converting enzyme 2 (ACE2) (Lan J et al., 2020, Nature 581:215-220). Despite these similarities, the new coronavirus spreads more widely and rapidly, and is more lethal than SARS viruses (Zhu N et al, 2020, N Engl J Med, 382:727-733). Therefore, there is an urgent need to develop a safe, efficient and inexpensive SARS-CoV-2 vaccine to effectively combat the spread of the new coronavirus. During the early development of vaccines against SARS-CoV, researchers found that antibodies against the viral spike protein (S protein) were highly effective in neutralizing the virus and preventing infection (Yang Z Y et al., 2005, Proc Natl Acad Sci USA 102:797-801), and therefore, the S protein of SARS-CoV-2 is the prime target for current antiviral drug and vaccine development (Walls A C et al., 2020, Cell 181:281-292.e6).

Currently, multiple research institutes and pharmaceutical companies are moving rapidly to develop new coronavirus vaccines, including live attenuated vaccines, recombinant virus vector vaccines, inactivated virus vaccines, protein subunit vaccines, virus-like particle (VLP) vaccines, and nucleic acid vaccines (Jeyanathan M et al., 2020, Nat Rev Immunol 20: 615-632). Although live attenuated vaccines show high protective power, they are associated with high risks; inactivated vaccines, recombinant viral vaccines and nucleic acid vaccines face high costs and inconvenience in vaccination; and direct administration of traditional recombinant protein vaccines does not provide good protection because they do not stimulate cellular immune responses well and often require the addition of adjuvants (Guy B et al, 2007, Nat Rev Microbiol 5: 505-517). To date, all vaccines developed domestically and internationally are administered by injection, and side effects of the new coronavirus vaccines have been reported in several countries, even leading to deaths. Injection is the most direct route of administration; however, it is also the riskiest and most expensive route of administration. Heretofore, there is a lack of other more convenient and safer delivery methods or routes of administration in the development of new coronavirus vaccines.

Vaccine works as follows: when vaccine antigen is inoculated into an animal body, the immune system of the animal body is stimulated, and the antigen-presenting cells of the animal body process and present the vaccine to specific lymphocytes (T and B lymphocytes). Then, the lymphocytes recognize, activate, proliferate, differentiate the vaccine and finally produce immune effector molecules (antibodies and cytokines) and immune effector cells, and finally remove the antigen from the animal body. This process is called the immune response. Thus, it can be seen that currently, the common method of administering antigen by injection around the world in the development of new coronavirus vaccines may lead to some possible side effects of the antigen in systemic tissues. The process of vaccine-induced immunity is actually generated through antigen-presenting cells. Therefore, if antigen is restricted to be produced in antigen-presenting cells, it is possible to limit the possible side effects of antigen in systemic tissues and achieve the goal of greater safety.

Oral vaccines based on attenuated strains are widely used in the development of vaccines for a variety of infectious diseases due to the advantages of simple vaccination and low cost. As a widely used bacterial oral vaccine vector, attenuated *Salmonella* is also a natural mucosal immune adjuvant and an antigen expression and delivery vehicle. Genetically engineered recombinant vaccine strains enter the body through M cells in the intestine after oral gavaging (Jensen V B et al., 1998, Infect Immun 66:3758-3766). The strains that have entered the body environment can be phagocytosed rapidly by antigen-presenting cells (APCs), and if at this moment, with the aid of the bacterial secretion system, the antigenic proteins can be effectively secreted into the APCs. Finally, the antigenic proteins were effectively broken down into peptides and presented to the T-help cells via the histocompatibility complex MHC-I or MHC-II pathway to stimulate cellular, humoral, and mucosal immune responses of the body against antigenic molecules (Mei Y et al., 2017, Cancer Immunol Res 5:503-514).

However, the development of an efficient and highly applicable oral attenuated *Salmonella* vaccine for the prevention of the new coronavirus still faces the following technical challenges: a) maintaining the phenotypic stability of the recombinant bacteria and using attenuated bacteria as an expression tool for exogenous antigens require establishment of a suitable expression strategy to optimize the antigen expression and plasmid compatibility, otherwise there will be excessive strain virulence and severe loss of engineered plasmids, which results in loss of immune effect; b) the effectiveness of antigen protein secretion into the cells via the thallus, because most bacteria are wrapped in a membrane-encapsulated vesicle structure (SCV) after entering the antigen-presenting cells, which largely limits the effective presenting of antigen molecules (Zhang X L et al., 2008, Cell Mol Immunol 5:91-97), and failure to achieve effective presentation will greatly reduce the preventive effect of the vaccine; c) the selection of a promoter that allows the antigen molecules to be expressed only in antigen-presenting cells but not in blood and normal tissues, thereby providing safety for the antigen molecules; and d) the optimality of viral antigen epitope screening and domain selection. Due to the large molecular weight and complex structure of the new coronavirus S protein (Hsieh C L et al. 2020, Science 369: 1501-1505), screening of different epitopes of its multiple structural domains is required to avoid overly complex protein structures that cannot be efficiently secreted and to induce a better immune response by presenting as many effective antigenic determinants as possible.

Therefore, to obtain an efficient coronavirus (SARS-CoV-2) vaccine based on an attenuated *Salmonella* secretory expression system, a safe, efficient and stable *Salmonella* secretory expression vector must be constructed to ensure that antigen molecules can be expressed in *Salmonella* and effectively secreted into antigen-presenting cells to efficiently induce an immune response in the body. This is the problem to be solved by the present invention.

The hydrophobic properties and charge distributions of different proteins vary greatly because different proteins have different primary sequences, and different primary sequences of different proteins lead to different spatial structures or higher-level structures, resulting in greatly different spatial conformations of the proteins and greatly different physical and chemical properties of protein surfaces. Therefore, it is extremely difficult to achieve efficient and stable secretory expression of different antigenic proteins in *Salmonella*, and they are not predictable or deducible, and creative efforts will be needed to study and explore them one by one.

More importantly, with respect to the new coronavirus S protein, a multidomain, very large molecular weight protein, the number of amino acids in the mature protein is over 1368 amino acid residues, and different antigenic epitope clusters are located in different structural domain segments at different spatial locations. When the S protein is used as a coronavirus vaccine, the common approach of all developed vaccines is to use the whole protein as a vaccine in combination with an adjuvant, regardless of whether the specific vaccine is a protein vaccine, a viral vaccine, or a nucleic acid vaccine. However, if each subunit of the S protein is separately enhanced with an adjuvant and then different subunit vaccines are used in combination, will the immune effect of each subunit vaccine be fully and better exhibited? Theoretically, the immune effect of combined subunit vaccines should be better than that of the route where the whole protein is used as a single immunization unit.

However, this route is difficult in practice because, theoretically, it is more expensive to develop and prepare and technically more complicated. One aspect of the present invention is to provide a new route for the development of a coronavirus vaccine, which has not been tried thus far around the world. The route of the present invention is simple, inexpensive and safe.

SUMMARY OF THE INVENTION

The main objectives of the present invention are to construct an efficient vector in which the secretory expression of attenuated *Salmonella* in antigen-presenting cells can be controllable, to screen out the antigenic epitope structural domains of the coronavirus that can induce the best immune response and to develop a single antigenic structural domain vaccine of the coronavirus with attenuated *Salmonella* as the transport vector, which has stable expression, good safety and good protection. On this basis, the strains of attenuated *Salmonella* vaccines expressing different single antigenic structural domains of the coronavirus are mixed together to develop an oral coronavirus vaccine with stable expression, good safety and high protection.

To achieve the above objectives, the present invention provides the following technical solution: A new coronavirus vaccine based on controllable secretory expression of attenuated *Salmonella*, comprising an antigen expression vector and an antigen presentation system for the new coronavirus vaccine.

Furthermore, the antigen presentation system is an oral vaccine presentation system with an intracellularly induced secretory expression adapted to different structural domains of the S protein in the attenuated *Salmonella* antigen-presenting cells; the antigen expression vector and the antigen presentation system for the new coronavirus vaccine is a *Salmonella* type III antigen secretory expression system induced by the intracellular environment of the antigen-presenting cells, and the *Salmonella* type III antigen secretory expression system comprises a type III secretion system promoter and a signal peptide sequence.

Based on the analysis of the intracellular microenvironment of antigen-presenting cells such as macrophages, the present invention uses a bioinformatic approach and molecular cloning technology to clone bacterial promoters and secretion signals. For each single antigenic structural domain of the new coronavirus, the intracellular inducible promoter is used to regulate the bacterial secretion signal to secrete and express the antigen of this structural domain, and plasmid anti-loss elements are added to improve intracellular plasmid stability to construct an efficient and stable intracellularly regulated orally administered antigen presentation system for the secretion and expression of a single antigenic structural domain in attenuated *Salmonella*.

The present invention provides an orally administered new coronavirus vaccine presentation system for attenuated *Salmonella*-induced secretory expression, wherein based on the gram-negative bacteriophage type III secretion system capable of secreting a single antigenic structural domain of the new coronavirus, a type III secretion signal is fused with a structural domain antigenic molecule to achieve secretion of the antigen of the new coronavirus. The type III secretion signal is a *Salmonella* virulence island 2 (SPI-2) effector protein SseJ, and a SseJ promoter or a SifB promoter is used to regulate the expression thereof; the structural domain antigen molecule is part or full of amino acid sequences of NTD, RBD, and S2 structural domains of the SARS-CoV-2 spike protein (S protein). After numerous comparative experiments, the system has been proven applicable to the secretion and expression of the three structural domains of different sizes, structures and functions.

The present invention provides an orally administered vaccine presentation system of attenuated *Salmonella* antigen-presenting cells intracellularly induced secretory expression adapted to different structural domains of the S protein, wherein the system is a *Salmonella* type III antigen secretory expression system induced by the intracellular environment of the antigen-presenting cells, and the expression system comprises a type III secretion system promoter and a signal peptide sequence.

Different attenuated *Salmonella* antigen-presenting strains, that can express different antigenic structural domain proteins of the new coronaviruses by intracellular secretion in a controllable manner, are mixed to prepare an efficient, safe, antigen-presenting cell intracellularly expressed, inexpensive and convenient new coronavirus vaccine.

Furthermore, the present invention constructs attenuated *Salmonella* antigen-presenting strains with controllable, stable and efficient intracellular secretory expression of different antigenic structural domain proteins of the coronavirus.

Furthermore, an inducible promoter in the antigen-presenting cells is used to regulate the antigen secretion expressed by a bacterial secretion signal, the Salmonellas secretory expression system is used to achieve antigen secretion, and a plasmid anti-loss element is added to improve the plasmid stability of the expression vector in the *Salmonella* cells, thereby achieving efficient, stable, antigen-presenting cells intracellularly regulated secretory expression of different antigen structural domains in attenuated *Salmonella* cells.

A further aspect is a combination of selected new coronavirus antigenic epitope structural domains that can induce an optimal immune response.

A further aspect is that the combination of the new coronavirus antigenic epitope structural domains that can induce an optimal immune response is the SARS-CoV-2 spike protein (S protein) RBD structural domain located at positions 319-541 of the full amino acid sequence of the S protein, and the RBD structural domain has a gene sequence of the nucleotide sequence shown in SEQ ID No. 6; or the combination of the new coronavirus antigenic epitope structural domains that can induce an optimal immune response is the SARS-CoV-2 spike protein (S protein) NTD structural domain located at positions 13-303 of the full amino acid sequence of the S protein, and the NTD structural domain of the ARS-CoV-2 spike protein has a gene sequence of the nucleotide sequence shown in SEQ ID No. 7; or the combination of the new coronavirus antigenic epitope structural domains that can induce an optimal immune response is part of the sequence of the SARS-CoV-2 spike protein (S protein) S2 structural domain located at positions 886-1077 of the full amino acid sequence of the S protein, and the S2 structural domain has a gene sequence of the nucleotide sequence shown in SEQ ID No. 8.

As a further aspect, the intracellularly inducible promoter in the antigen-presenting cells is the *Salmonella* sifB promoter with a gene sequence of the nucleotide sequence shown in SEQ ID No. 4; the plasmid anti-loss element is the AT element sequence with a gene sequence of the nucleotide sequence shown in SEQ ID No. 10, thereby achieving continuous and stable expression of the antigen and efficient capture, identification and presentation of the antigen by the antigen-presenting cells in the body.

Furthermore, the secretory expression system containing the bacterial secretion signal is a *Salmonella* type III secretory expression system. The *Salmonella* type III secretion signal is the *Salmonella* virulence island 2 (SPI-2) effector protein SseJ signal peptide with a gene sequence of the nucleotide sequence shown in SEQ ID No. 5. Expression of multiple vaccine antigens is achieved by attenuated *Salmonella*, and the attenuated *Salmonella* is VNP20009, htrA gene-deficient attenuated *Salmonella* VNP20009 (Ah-1), or other attenuated *Salmonella*.

As a further aspect, a vaccine of strain mixture of multiple recombinant attenuated *Salmonella* is prepared and the strain mixture comprises two recombinant attenuated *Salmonella* strains loaded respectively with Ah-BJ-RBD and Ah-BJ-NTD expression plasmids. The strain mixture comprises at least two of the above-mentioned strains.

Use of the method of preparation of a new coronavirus vaccine based on controllable secretory expression of attenuated *Salmonella* of the present invention for inducing a body to produce high potency antibodies in a mouse model by oral gavaging of a strain mixture of attenuated *Salmonella* comprising an expression vector of the new coronavirus vaccine antigen.

Use of the method of preparation of a coronavirus vaccine based on controllable secretory expression of attenuated *Salmonella* of the present invention in preparation of a new coronavirus vaccine or a new coronavirus preventive drug.

The present invention provides a new method of preparing a new coronavirus vaccine, specifically, by mixing recombinant *Salmonella* strains expressing different antigenic structural domains of the SARS-CoV-2 spike protein (such as NTD, RBD, S2, etc. The RBD structural domain is located at positions 319-541 of the full amino acid sequence of the S protein; part of the sequence of the S2 structural domain is located at positions 886-1077 of the full amino acid sequence of the S protein; and the NTD domain is located at positions 13-303 of the full amino acid sequence of the S protein in a certain ratio to make a mixed bacterial vaccine to induce an optimal immune response after vaccination, thereby providing efficient protection.

Beneficial effect: The present invention provides a method of preparation of an efficient, safe, antigen-presenting cell intracellularly expressed, inexpensive and convenient new coronavirus vaccine that is usable for humans and animals and the uses thereof. The present invention constructed controllable and stable expression plasmids for secretory expression of different antigenic structural domain proteins of the new coronavirus and their attenuated *Salmonella* expression strains, and then mixed various attenuated *Salmonella* antigen-presenting strains that can achieve controllable intracellular secretory expression in antigen-presenting cells. By oral gavage with aid of the unique secretion system, a variety of different antigenic proteins can be secretory-expressed efficiently in antigen-presenting cells after oral gavaging. The secretory-expressed antigenic proteins can be efficiently processed and presented by the antigen-presenting cells and finally activate/regulate the immune system to produce more potent antibodies to make the vaccine work.

Compared to existing vaccines and vaccines being developed for the new coronavirus, the features and innovations of the present invention are as follows:

1) The present invention uses *Salmonella* type III secretion system signals to regulate the new coronavirus vaccine antigen expression vector to achieve controllable secretory expression of antigen molecules of different structural domains of the new coronavirus, and induces the production of high potency antibodies in the bodies of a mouse model.

2) The present invention provides a new method of preparing a new coronavirus vaccine with mixed strains. The vaccine prepared by the method uses new attenuated *Salmonella* as a vector, and due to its weak pathogenicity, the new attenuated *Salmonella* itself can serve as a highly effective adjuvant, which eliminates the need for an additional adjuvant and thus is safe and has few side effects.

3) The present invention provides a new coronavirus vaccine prepared using highly effective mixed strains, and the vaccine expresses multiple antigenic epitopes or structural domains of the new coronavirus using an attenuated *Salmonella* vector to enhance the immune response of a body to the vaccine, which overcomes the shortcoming of lacking a strong immune response due to insufficient presentation of the multiple structural domain epitopes when a single antigenic epitope/structural domain or multiple structural domain-containing proteins are expressed as a whole.

4) The present invention provides a low-cost method of preparing a new coronavirus vaccine with mixed strains, which uses new attenuated *Salmonella* as a vector to prepare the vaccine, and due to the self-proliferating characteristics of the attenuated strains, the production cost is low and the vaccine preparation time is greatly reduced, thereby simplifying the operation process and making the final product with a great price advantage.

5) The present invention provides a new coronavirus vaccine intracellularly expressed in antigen-presenting cells, which is only expressed intracellularly in antigen-presenting cells. Therefore, it can not only effectively produce the immune effect but also effectively avoid the presence of the antigen in normal tissues and possible side effects, thereby providing a higher safety level.

6) The present invention provides a safe and controllable orally administered vaccine system that uses new attenuated *Salmonella* as a vector and allows for effective and rapid regression by administration of conventional *Salmonella*-sensitive antibiotics.

7) Although the RBD, NTD and S2 structural domain recombinant engineered strains expressed and secreted these three structural domain proteins at the same level, and the amount of each recombinant strain was the same in all experimental groups, their individual immune effects and combined immune effect vary greatly, which could not be found by research and development with a single antigenic structural domain or based on theoretical prediction. This highlights the necessity and creativity of the present invention.

Figure 3:
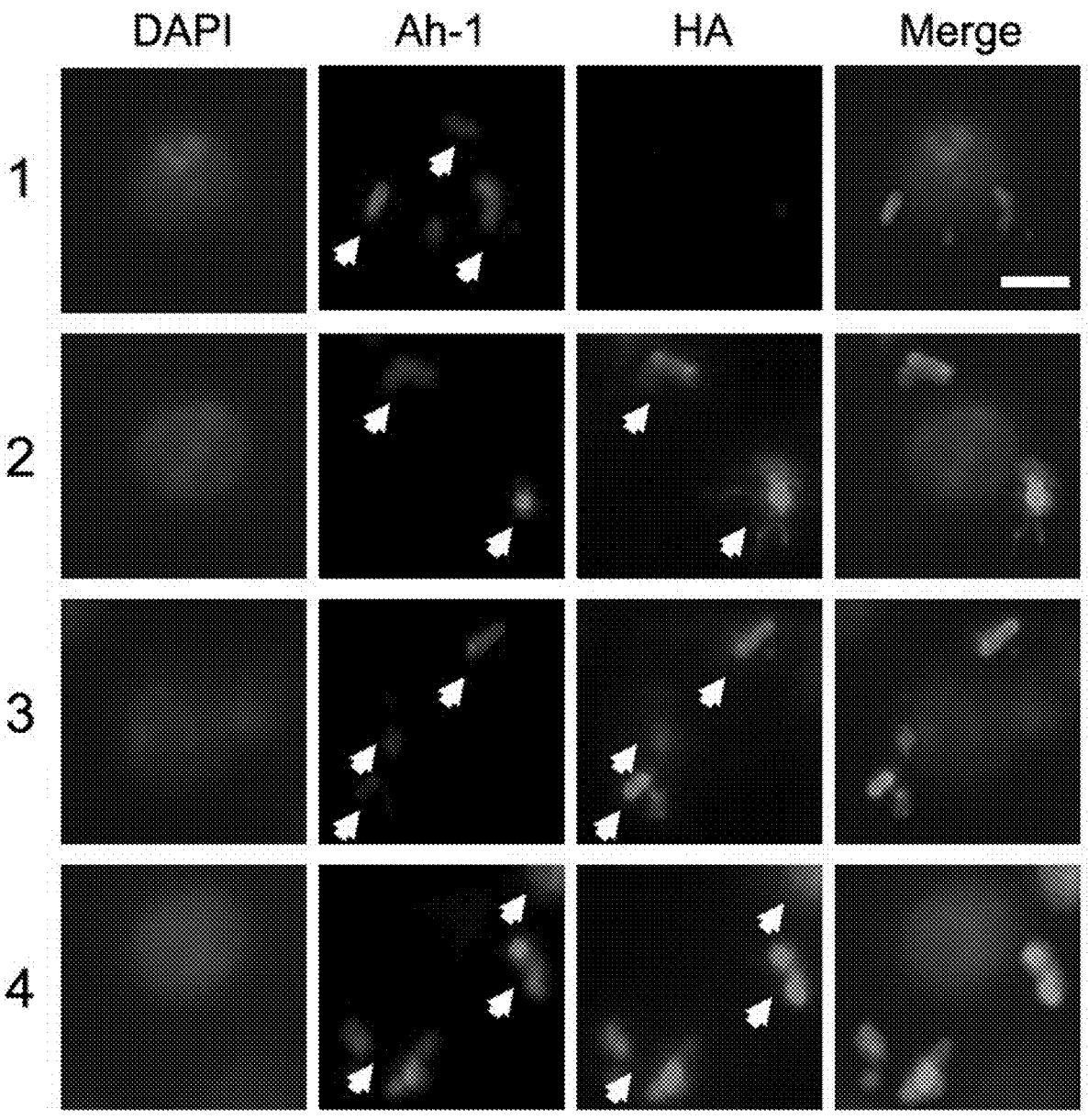

FIG. 3 shows the immunofluorescence detection of the recombinant attenuated *Salmonella* engineered bacteria of the present invention for intracellular expression and secretion of RBD, NTD, and S2 structural domain proteins in macrophages. 1. Recombinant attenuated *Salmonella* loaded with an expression plasmid that does not contain a protein sequence and an HA tag, but the remaining components are the same; 2. Ah-BJ-RBD recombinant attenuated *Salmonella;* 3. Ah-BJ-NTD recombinant attenuated *Salmonella;* 4. Ah-BJ-S2 recombinant attenuated *Salmonella*. DAPI was used to stain the nuclei, Ah-1 was stained by *Salmonella* fluorescent antibody (at the arrowheads), and RBD-HA, NTD-HA, and S2-HA were stained by HA-tagged fluorescent antibody (at the arrowheads). All three recombinant attenuated *Salmonella* engineered bacteria expressed and secreted the RBD, NTD, and S2 structural domain proteins intracellularly in macrophages. The levels of expression and secretion of these three structural domain proteins by the recombinant engineered bacteria expressing the RBD, NTD, and S2 structural domains were compared using the same HA antibody, and the results showed that the recombinant engineered bacteria for the RBD, NTD, and S2 structural domains expressed and secreted these three structural domain proteins at the same level.

Figure 4A:
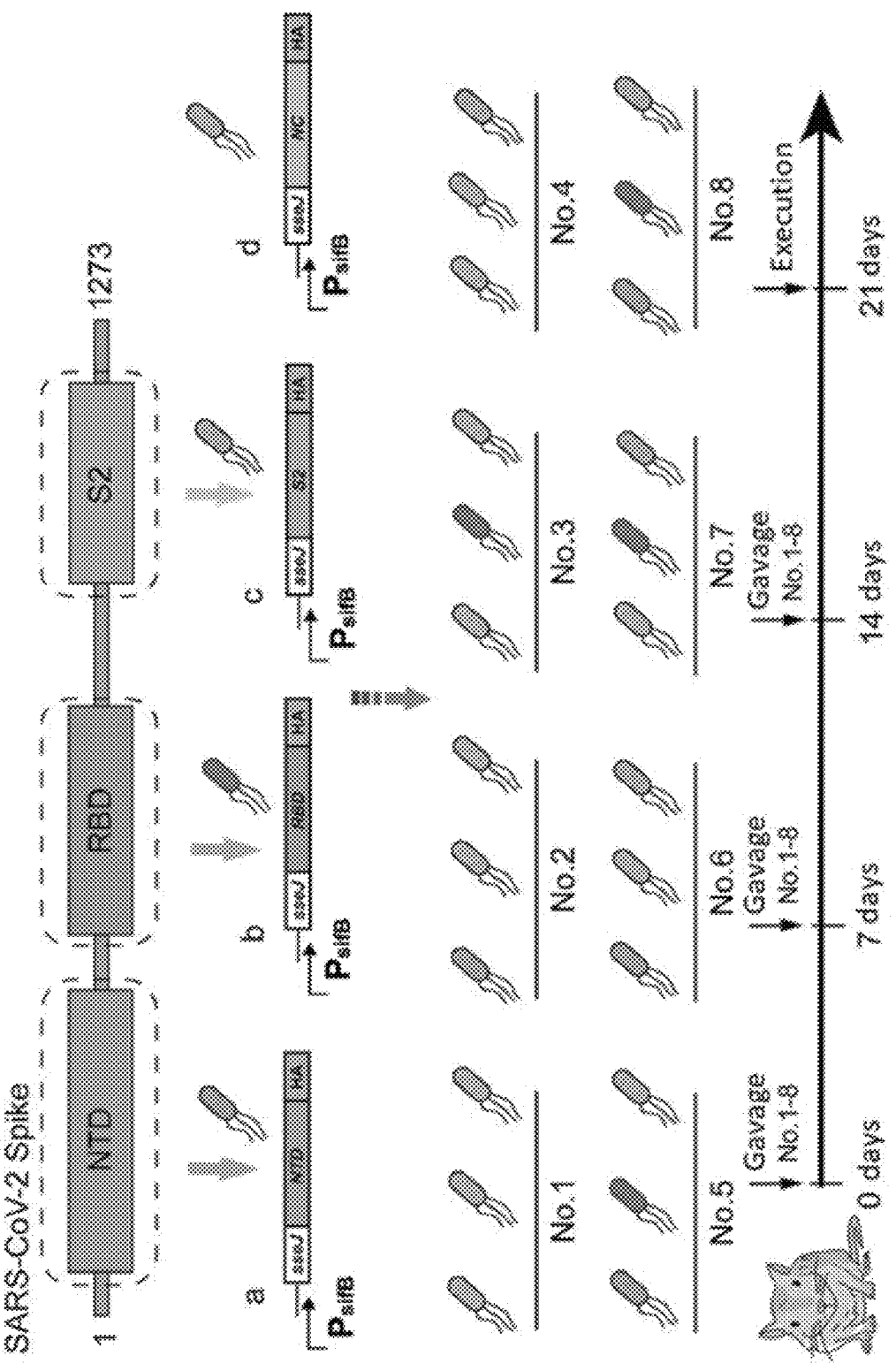
Figure 4B:
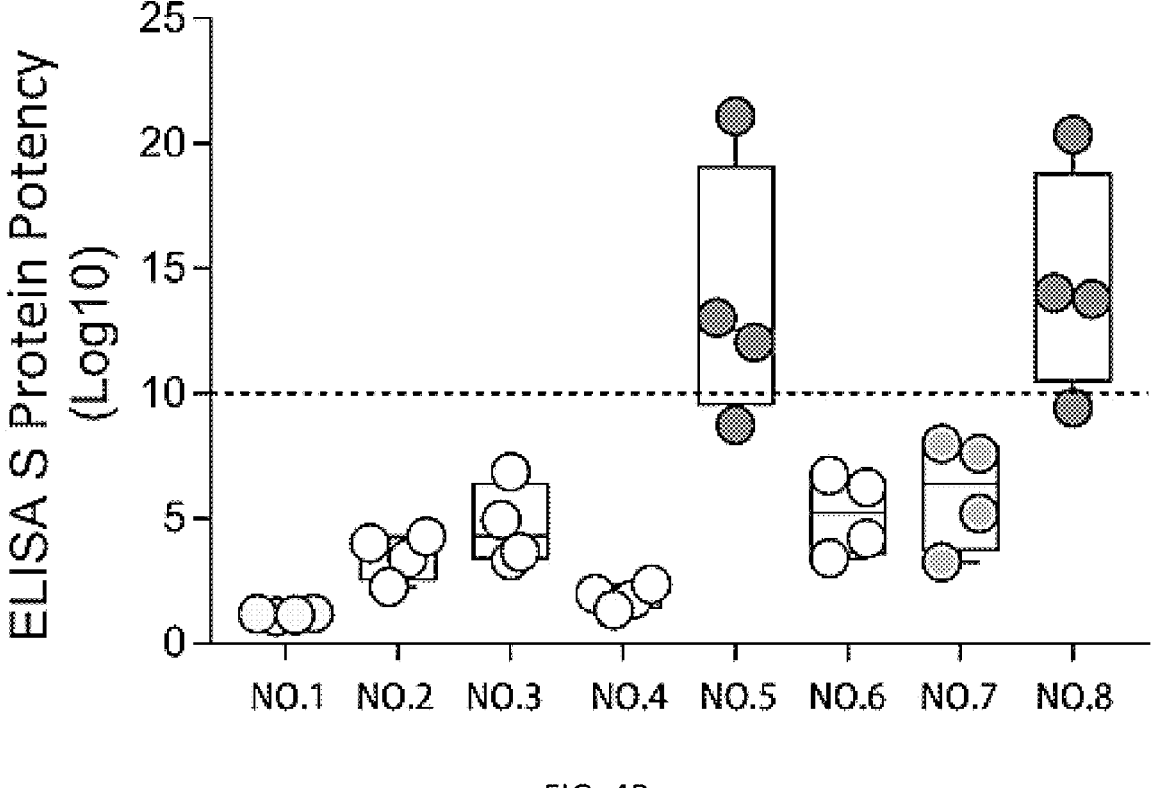

FIGS. 4A and 4B show the evaluation of the oral gavage of the new coronavirus vaccine prepared from the recombinant attenuated *Salmonella* mixture of the present invention for induced antibody production, wherein FIG. 4A shows a schematic diagram of the experimental design of gavage administration to mice of the new coronavirus vaccine prepared with different recombinant attenuated *Salmonella* mixtures of the present invention. a. Recombinant attenuated *Salmonella* containing Ah-BJ-RBD; b. recombinant attenuated *Salmonella* containing Ah-BJ-NTD; c. recombinant attenuated *Salmonella* containing Ah-BJ-S2; d. recombinant attenuated *Salmonella* containing Ah-BJ-NC *Salmonella*. No. 1: d+d+d; No. 2: a+d+d; No. 3: d+b+d; No. 4: d+d+c; No. 5: a+b+d; No. 6: a+d+c; No. 7: d+b+c; No. 8: a+b+c, and FIG. 4B shows a comparison of the potency of inducing S protein antibody in mice of the new coronavirus vaccines prepared with different recombinant attenuated *Salmonella* mixtures of the present invention. No. 1: d+d+d; No. 2: a+d+d; No. 3: d+b+d; No. 4: d+d+c; No. 5: a+b+d; No. 6: a+d+c; No. 7: d+b+c; No. 8: a+b+c.

DETAILED DESCRIPTION OF THE INVENTION

The present invention will be described in detail below in conjunction with the accompanying drawings and specific embodiments. The following embodiments are used to illustrate the present invention but are not intended to limit the scope thereof. The S protein domain (including RBD, NTD, and S2) of the new coronavirus SARS-CoV-2 is used as the antigen to be presented in the Examples. The attenuated *Salmonella* used in the Examples is the htrA gene-deficient VNP20009 attenuated strain (referred to as Ah-1). Where specific conditions are not indicated in the Examples, conventional conditions or those recommended by the manufacturer are followed.

Figure 1:
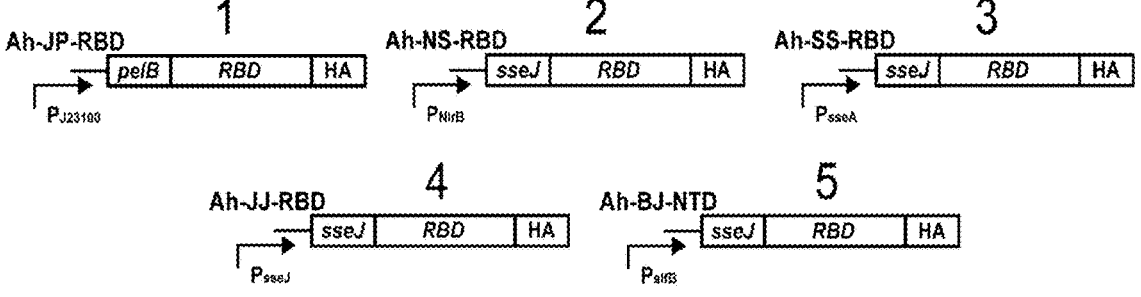
FIG. 1 shows a schematic diagram of the different expression systems constructed for the RBD structural domain of the new coronavirus of the present invention. 1. Ah-JP-RBD plasmid, using the J23100 promoter and PelB signal peptide to express the RBD protein; 2. Ah-NS-RBD plasmid, using the NirB promoter and the SseJ signal peptide to express the RBD protein, wherein the NirB promoter has the gene sequence of the nucleotide sequence shown in SEQ ID No. 1; 3. Ah-SS-RBD plasmid, using the SseA promoter and the SseJ signal peptide to express the RBD protein, wherein the SseA promoter has the gene sequence of the nucleotide sequence shown in SEQ ID No. 2; 4. Ah-JJ-RBD plasmid, using the SseJ promoter and the SseJ signal peptide to express the RBD, wherein the SseJ promoter has the gene sequence of the nucleotide sequence shown in SEQ ID No. 3; 5. Ah-BJ-RBD plasmid, using the SifB promoter and the SseJ signal peptide to express the RBD protein. Three recombinant attenuated *Salmonella* species, Ah-JP-RBD, Ah-JJ-RBD and Ah-BJ-RBD, all effectively induced the production of corresponding antibodies in the body, with Ah-BJ-RBD recombinant attenuated *Salmonella* significantly better than the other three recombinant species in terms of antibody production. Compared to those of the Ah-NC, Ah-JP-RBD and Ah-JJ-RBD recombinant attenuated *Salmonella* species, the antibody titer of the Ah-BJ-RBD recombinant attenuated *Salmonella* exhibited an increase by 6.03, 3.55 and 2.19 times, respectively.

Example 1. Construction of Antigenic Protein (New Coronavirus Protein RBD)-Presenting Plasmid RBD is part of the structural domain of the new coronavirus S protein, and structural analysis shows that the RBD protein plays a key role in the binding of the S protein to ACE2 (angiotensinase 2). In view of the larger structural domain of S, after extensive and multifaceted bioinformatics analysis and cross-comparison mapping and prediction, it was found that the RBD located at positions 319-541 of the amino acid sequence of the S protein contains more antigenic determinant sites. With extensive experimental studies regarding various commonly reported bacterial secretion systems, secretion signal peptides and matching promoters, the present invention chose to use the strong constitutive promoter J23100 and the PelB signal peptide after screening the constitutively expressed secretion system Ah-JP-RBD plasmid. With respect to the inducible type III secretory expression plasmids Ah-NS-RBD, Ah-SS-RBD, Ah-JJ-RBD and Ah-BJ-RBD, the present invention has tried separately to use the hypoxia promoter NirB and type III secretion system-related promoters SseA, SseJ and SifB, and all four plasmids used the type III secretion system-related signal peptide SseJ. The N-termini of the above five plasmids were coupled to the antigenic molecule NTD protein sequence with the aid of a linker to achieve secretion. The RBD was coupled to the HA tag for convenience of subsequent detection (FIG. 1). The gene sequence of the linker is the nucleotide sequence shown in SEQ ID No. 9.

NirB, SseA, SseJ and SifB promoters, SseJ, PelB signal peptides, and RBD in the S protein domain of SARS-CoV-2 were obtained by PCR. The relevant primer sequences are as follows:

PNirB P1: The gene sequence of the PNirB P1 primer is the nucleotide sequence shown in SEQ ID No. 11.

PNirB P2: The gene sequence of the PNirB P2 primer is the nucleotide sequence shown in SEQ ID No. 12.

PSseA P1: The gene sequence of the PSseA P1 primer is the nucleotide sequence shown in SEQ ID No. 13.

PSseA P2: The gene sequence of the PSseA P2 primer is the nucleotide sequence shown in SEQ ID No. 14.

PSifB P1: 5'-caaaatcccttataagaattctgccctaccgctaaacatc-3'; the gene sequence of the PSifB P1 primer is the nucleotide sequence shown in SEQ ID No. 15.

PSifB P2: 5'-tgtccaacactcaatggcatccacaagtgattatgata-3'; the gene sequence of the PSifB P2 primer is the nucleotide sequence shown in SEQ ID No. 16.

SseJ P1: 5'-tatcatataatcacttgtggatgccattgagtgttggaca-3'; the gene sequence of the SseJ P1 primer is the nucleotide sequence shown in SEQ ID No. 17.

SseJ P2: 5'-gccttcagtggaataatgatgagctataaaactttctaac-3'; the gene sequence of the SseJ P2 primer is the nucleotide sequence shown in SEQ ID No. 18.

PSseJ-sseJ P1: 5'-caaaatcccttataagaatttcacat-aaaacactagcact-3'; the gene sequence of the PSseJ-sseJ P1 primer is the nucleotide sequence shown in SEQ ID No. 19.

PSseJ-sseJ P2: 5'-gccttcagtggaataatgatgagc-tataaaacttctaac-3'; the gene sequence of the PSseJ-sseJ P2 primer is the nucleotide sequence shown in SEQ ID No. 20.

Fifty nanograms of Salmonella genomic DNA was used as the template.

RBD P1: 5'-agcggaggtggcaggcagcccgaacatcaccaacctg-3'; the gene sequence of the RBD P1 primer is the nucleotide sequence shown in SEQ ID No. 21.

RBD P2: 5'-tctggaacatcgtatgggtacggcgcgtgcagcagttc-3'; the gene sequence of the RBD P2 primer is the nucleotide sequence shown in SEQ ID No. 22.

Commercial plasmid MC_0101082 was used as a template; Vec P1: 5'-tacccatacgatgttccagattacg-3'; the gene sequence of the RBD P2 primer was the nucleotide sequence shown in SEQ ID No. 23.

Vec P2: 5'-gctgcctccacctccgctgc-3'; the gene sequence of the RBD P2 primer is the nucleotide sequence shown in SEQ ID No. 24.

The plasmid pQE30 with the AT element from our lab was used as the template. The linker sequence between the signal peptide and the target protein was obtained using the thermal annealing self-association method. After obtaining the individual fragments by PCR, the corresponding fragments were assembled using the homologous recombination method to finally obtain various protein expression secretion vectors of the type III secretion system, including Ah-JP-RBD, Ah-NS-RBD, Ah-SS-RBD, Ah-JJ-RBD, and Ah-BJ-RBD.

Example 2. Electroporation Transformation of Recombinant Attenuated Salmonella

Preparation of electroporation-competent Salmonella: Fresh attenuated Salmonella was inoculated into 200 mL LB medium, incubated in a shaker at 37° C. until the OD value was between 0.4-0.6, centrifuged at 5,000 rpm for 5 min to collect the bacteria, washed once with sterile double-distilled water, and centrifuged at 5,000 rpm for 5 min, and the bacteria were washed with sterilized 10% glycerol 3-5 times, centrifuged at 5,000 rpm for 5 min, resuspended in 500 μL of 10% glycerol, and then portioned as 50 μL/tube for electroporation transformation. The recombinant vaccine DNA vector was transformed into attenuated Salmonella by the electroporation method: 0.5-5 μg of the constructed recombinant vector was added to the electroporation-competent state under aseptic conditions, mixed evenly, and transferred to a 2 mm electroporation transformation cup for electroporation at 1.8 kV, 25 μF and 500Ω. After electroporation transformation, the vector was coated onto a kanamycin plate for screening. The grown colonies were the constructed recombinant bacteria, and monoclonal strains were selected for sequencing.

Example 3. Effective Secretion Detection of Antigenic Proteins

The obtained recombinant attenuated Salmonella was cultured in kanamycin-resistant liquid LB medium until the OD600 value was 0.8-1.0. The bacteria were collected, and the OD600 value was adjusted to approximately 1.0 with PBS and placed at 4° C. for use. The macrophage line RAW264.7 was induced using 100 ng/mL LPS for 24 hr to obtain M1-type macrophages (referred to as RAW264.7 (M1) below). The obtained RAW264.7 cells (M1) were cocultured with the four recombinant attenuated Salmonella bacteria Ah-NS-RBD, Ah-SS-RBD, Ah-JJ-RBD, and Ah-BJ-RBD at 1:10 for 90 min. The supernatant was removed, washed 2-3 times with PBS, and cultured in cell culture medium (10% serum, without double antibodies) supplemented with 100 ng/ml gentamicin for 6 hr. Cells were collected, and total cellular proteins were collected by thermal lysis, i.e., cells were resuspended in 100 μL PBS, 25 μL 5× loading buffer was added, and then lysed at 100° C. for 10-15 min. After centrifugation at 9,000 rpm for 5 min, the four recombinant bacteria in LB were collected, and total proteins were collected from the cells using the same method.

For Ah-JP-RBD recombinant attenuated Salmonella, the inoculated cells were expansion cultured in 50 ml of kanaresistant liquid LB to an OD600 value of approximately 1.0. The total protein in the supernatant was collected using the trichloroacetic acid (TCA)-acetone precipitation method. Briefly, the supernatant was transferred to a 50 ml centrifuge tube and centrifuged for 10 min at 15,000 g and 4° C. using an ultracentrifuge. The supernatant was taken and transferred to a new 50 ml centrifuge tube, and 10% TCA was added thereto, swirled for full mixing, incubated on ice for 30 min and centrifuged again for 20 min at 7,000 g and 4° C. The precipitate was resuspended in 300 μL of PBS and then transferred to a 1.5 mL sterile EP tube. Then, 1.2 mL precooled acetone (−20° C.) was added, and the mixture was centrifuged for 20 min at 17,000 g and 4° C. The supernatant was removed. Then, 300 μL of PBS was further added, and the above operations were repeated. The supernatant was removed. Forty microliters of PBS was added for resuspension, and the total protein secreted into the supernatant of the cells was obtained. After the cells collected by centrifugation were added to the loading buffer, they were boiled at 100° C. for 10 min to obtain the total protein of the cells. The collected total protein was detected using protein immunoblotting (WB) to determine whether target proteins were produced and secreted. Rabbit monoclonal HA tag antibody was used as the primary antibody, and a goat anti-rabbit IgG antibody coupled with HRP was used as the secondary antibody.

The detection results showed that Ah-JP-RBD recombinant attenuated *Salmonella* was able to express and secrete the RBD protein efficiently, while for the four recombinant attenuated *Salmonella* species Ah-NS-RBD, Ah-SS-RBD, Ah-JJ-RBD and Ah-BJ-RBD, none of the four species showed expression and secretion of RBD protein when the cells were present in liquid LB. However, when the cells were inside the macrophage and stimulated by the induction of the intracellular environment, both Ah-JJ-RBD and Ah-BJ-RBD recombinant attenuated *Salmonella* effectively expressed larger bands of RBD protein with signal peptide, and after the protein had been effectively secreted into the interior of the cells, the signal peptide was sheared off, thus presenting an RBD protein band with a smaller molecular weight. The expression and secretion of RBD protein were not effectively achieved in either Ah-NS-RBD- or Ah-SS-RBD-engineered bacteria.

Example 4. Immunization Procedure and Method

Six- to eight-week-old female C57BL/6 mice were grouped as 4-5 mice per group, and each mouse was inoculated orally at a dose of $10\times10^9$ CFU with empty cells or 3 recombinant attenuated *Salmonella* species, Ah-JP-RBD, Ah-JJ-RBD and Ah-BJ-RBD, at an interval of one week, and eye blood sampling was performed one week after the third inoculation to detect the specific antibody concentration in the serum.

Example 5. Detection of Antibodies Against the RBD Structural Domain Protein of the New Coronavirus S Protein Preparation of immune serum: After obtaining the blood from the immunized mice as described above, the blood was left at room temperature for 2-4 hr and centrifuged at 3,000 rpm and 4° C. for 15 min, and the serum was collected and stored at −80° C.

ELISA determination of total IgG antibody titer: 1. Antigen coating: 50 mM, pH 9.6 carbonate buffer was used to dilute the recombinant S protein antigen of SARS-CoV-2 at 10 μg/mL, and 100 μL was added dropwise to each well. The ELISA plate was coated at 4° C. overnight and then washed three times (once every 5 min) with PBST. 2. Blocking: 300 μL of 3% BSA was added to each well of the coated plate, and the coated plate was blocked at 37° C. for 3 hr and then washed three times (once every 5 min) with PBST. 3. Loading: the serum was added to the wells after the serum gradient was diluted (50-400 times) using 100 μL of PBS, reacted at 37° C. for 1-2 hr and then washed three times (once every 5 min) with PBST. 4. Secondary antibody: HRP (horseradish peroxidase)-coupled goat anti-mouse IgG secondary antibody (PBST 1: 5000 dilution) was added, reacted for 1 hr at 37° C., and washed three times (once every 5 min) with PBST. 5. Color developing: after plate washing, 100 μL of TMB substrate solution was added, and the color was developed for 5-10 min at room temperature. When the color became blue, 100 μL of 2M concentrated sulfuric acid was added to each well for termination, and then the 450 nM absorbance was measured.

The antibody potency assay results showed that all three recombinant attenuated *Salmonella* species, Ah-JP-RBD, Ah-JJ-RBD and Ah-BJ-RBD, effectively induced the production of corresponding antibodies against the RBD protein of the new coronavirus in mice, with the Ah-BJ-RBD recombinant attenuated *Salmonella* being significantly more effective than the other three recombinant species in inducing antibody production. Compared to Ah-NC, Ah-JP-RBD and Ah-JJ-RBD, Ah-BJ-RBD recombinant attenuated *Salmonella* species, the ELISA RBD protein titer of the Ah-BJ-RBD recombinant attenuated *Salmonella* was increased by 6.03, 3.55 and 2.19 times, respectively, indicating that this system is more efficient.

Example 6. Construction and Evaluation of Ah-BJ-NTD and Ah-BJ-S2 Recombinant Bacteria Based on the Ah-BJ-RBD System The NTD in the S protein domain and the S2 structural domain of the new coronavirus SARS-CoV-2 were obtained using PCR.

```
NTD P1:
5'-gcagcggaggtggaggcagcgtgaatctgaccacccgc-3';

NTD P2:
5'-tctggaacatcgtatgggtagctcttcagggtgcacttg-3';
```

S2 P1: 5'-agcggaggtggaggcagcggtgcgggtgcggcgctg-3'; the gene sequence of the S2 P1 primer is the nucleotide sequence shown in SEQ ID No. 25.

S2 P2: 5'-tctggaacatcgtatgggtacgccggcgcggtggtaaagt-3'; the gene sequence of the S2 P2 primer is the nucleotide sequence shown in SEQ ID No. 26.

Commercial plasmid MC_0101082 was used as the template.

Vec P1: 5'-tacccatacgatgttccagattacg-3'; the gene sequence of the Vec P1 primer is the nucleotide sequence shown in SEQ ID No. 27.

Vec P2: 5'-gctgcctccacctccgctgc-3'; the gene sequence of the Vec P2 primer is the nucleotide sequence shown in SEQ ID No. 28.

Figure 2:
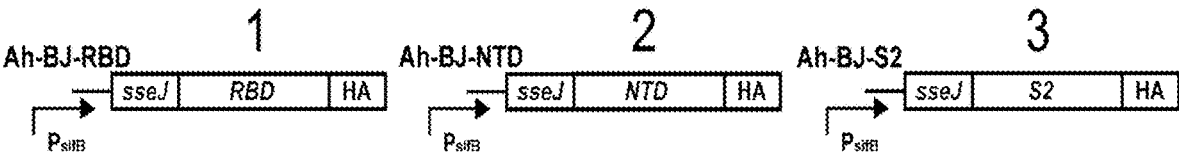
FIG. 2 shows a schematic diagram of the controllable secretory expression systems constructed for the RBD, NTD, and S2 structural domains of the new coronavirus of the present invention. 1. Ah-BJ-RBD plasmid, using the SifB promoter and the SseJ signal peptide to express the RBD structural domain protein. 2. Ah-BJ-NTD plasmid, using the SifB promoter and the SseJ signal peptide to express NTD structural domain protein. 3. Ah-BJ-S2 plasmid, using the SifB promoter and the SseJ signal peptide to express the S2 structural domain protein. Western blot results showed that recombinant attenuated *Salmonella* engineered bacteria containing the three expression plasmids expressed and secreted RBD, NTD, and S2 structural domain proteins intracellularly in macrophages, but they were not expressed in LB medium.

Ah-BJ-RBD was used as the template. After obtaining the individual fragments by PCR, the corresponding fragments were assembled using the homologous recombination method to finally obtain NTD and S2 protein expression secretion vectors of the type III secretion system comprising Ah-BJ-NTD and Ah-BJ-S2 (FIG. 2). The obtained plasmids were subjected to electroporation transformation as described in Example 2 to obtain the corresponding Ah-BJ-NTD and Ah-BJ-S2 recombinant attenuated *Salmonella* strains. The expression and secretion of the recombinant attenuated *Salmonella*-associated proteins were detected according to the Ah-BJ-RBD detection method described in Example 3. WB detection results showed that both Ah-BJ-NTD and Ah-BJ-S2 recombinant attenuated *Salmonella* were able to efficiently express and secrete the NTD protein and the S2 protein.

Intracellular expression and secretion of antigenic proteins for Ah-BJ-RBD, Ah-BJ-NTD, and Ah-BJ-S2 recombinant bacteria were analyzed with the aid of immunofluorescence. After cells growing on a slide of RAW264.7 (M1) that had phagocytized Ah-BJ-RBD, Ah-BJ-NTD and Ah-BJ-S2 recombinant bacteria were obtained as described in Example 3, they were washed three times with PBS, and the cells were fixed at room temperature for 30 min using 4% paraformaldehyde and then washed three times with PBS. Room temperature perforation was performed for 30 min by PBS-configured 0.5% Triton X-100. The slides were washed three times with PBS, and then room temperature blocking was performed for 30 min using 3% BSA. After washing three times with PBS, the slides were incubated with rabbit monoclonal HA-tagged antibody as the primary antibody at 4° C. overnight. After washing three times with PBST, the slide was incubated in the dark for 1 hr with rabbit anti-monkey IgG and *Salmonella* fluorescent antibody. After washing three times with PBST, the nuclear dye DAPI was added, and then the cells were observed and photographed using fluorescence microscopy. The results of fluorescence photography showed that all three recombinant attenuated *Salmonella* species, Ah-BJ-RBD, Ah-BJ-NTD and Ah-BJ-S2 present inside the macrophages effectively expressed and secreted RBD-HA, NTD-HA and S2-HA proteins, while no HA-related fluorescence signal was detected in recombinant attenuated *Salmonella* carrying an empty plasmid vector (FIG. 3).

Example 7. Effectiveness of a Mixture of 3 Recombinant Attenuated *Salmonella* Species, Ah-BJ-RBD, Ah-BJ-NTD and Ah-BJ-S2, in the Preparation of a New Coronavirus Vaccine to Induce S Protein-Specific Antibody Production On the basis of Example 4, an empty bacteria and the three recombinant attenuated *Salmonella* species, Ah-BJ- RBD, Ah-BJ-NTD and Ah-BJ-S2, were mixed in permutations and combinations (FIG. 4A) and then administered as described in Example 4. Then, the production of S protein-specific antibody was detected for each group of induced mice as described in Example 5. The results showed that, compared to No. 1, No. 2, No. 3, No. 4, No. 6 and No. 7, No. 5 exhibited an increase by 12.02, 3.90, 2.90, 7.38, 2.67, and 2.28 times, respectively. Compared to No. 1, No. 2, No. 3, No. 4, No. 6 and No. 7, No. 8 exhibited increases of 12.63, 4.13, 3.06, 7.74, 2.81, and 2.40 times, respectively. That is, the three strains Ah-BJ-RBD+Ah-BJ-NTD+Ah-BJ-S2 and the three strains Ah-BJ-RBD+Ah-BJ-NTD+Ah-BJ-NC were more efficient in inducing the body to produce S protein-specific antibodies of the new coronavirus. Therefore, the use of recombinant strain mixtures in the preparation of a new coronavirus vaccine is a more efficient method of preparing a vaccine to induce antibody production, with the vaccine prepared by mixing two recombinant strains, Ah-BJ-RBD and Ah-BJ-NTD, exhibiting the best immune effect (FIG. 4B). The results of such combinations have never been reported thus far and exhibit great significance for the development of new coronavirus vaccines.

Although RBD, NTD and S2 structural domain recombinant strains expressed and secreted these three structural domain proteins at the same level, and the amount of each recombinant strain was the same in all experimental groups, their individual immune effects and combined immune effects varied greatly, which could not be found by research and development with a single antigenic structural domain or based on theoretical prediction. This highlights the necessity and creativity of the present invention.

The above description shows and describes the basic principle, the main features and the advantages of the present invention. One skilled in the art should understand that the present invention is not limited by the above embodiments, and what is described in the above embodiments and the specification is only to illustrate the principle of the present invention, and there will be various changes and improvements to the present invention without departing from the spirit and scope thereof. The scope of the present invention is defined by the appended claims, specification and the equivalents thereof.

What is claimed is:

1. A SARS-CoV-2 coronavirus vaccine based on secretory expression of attenuated *Salmonella*, comprising:
   an antigen expression vector and an antigen presentation system for the SARS-CoV-2 coronavirus vaccine,
   wherein the attenuated *Salmonella* is htrA gene-deficient attenuated *Salmonella* VNP20009 (Ah-1);
   wherein the antigen expression vector is an oral vaccine presentation system capable of secretory expression through a *Salmonella* type III secretory expression system induced by an intracellular environment of antigen-presenting cells, the *Salmonella* type III antigen secretory expression system comprises a type III secretion system promoter and a signal peptide sequence and a plasmid anti-loss element;

wherein the type III secretion system promoter comprises a sifB promotor having a gene sequence of the nucleotide sequence shown in SEQ ID No. 4, the signal peptide sequence comprises a SseJ signal peptide having a gene sequence of the nucleotide sequence shown in SEQ ID No. 5; and the plasmid anti-loss element is an AT element having a gene sequence of the nucleotide sequence shown in SEQ ID No. 10; and wherein the SARS-CoV-2 vaccine comprises a recombinant VNP20009 (Ah-1) strain that expresses a SARS-CoV-2 spike protein (S protein) RBD structural domain located at positions 319-541 of full amino acid sequence of the S protein, and the RBD structural domain has a gene sequence of the nucleotide sequence shown in SEQ ID No. 6.

2. A method of preparing the coronavirus vaccine based on secretory expression of attenuated *Salmonella* according to claim 1, comprising the steps of: mixing different attenuated *Salmonella* antigen-presenting strains that can express different antigenic structural domain proteins of the coronavirus by intracellular secretion to prepare the coronavirus vaccine.

3. A method of preparing the coronavirus vaccine based on secretory expression of attenuated *Salmonella* according to claim 1, comprising the steps of: constructing attenuated *Salmonella* antigen-presenting strains with controllable, stable and efficient intracellular secretory expression of different antigenic structural domain proteins of the coronavirus; using an intracellular inducible promoter to regulate a bacterial secretion signal to secrete and express the antigen, using the *Salmonella* secretory expression system to obtain secretion of the antigen, and adding a plasmid anti-loss element to improve plasmid stability of the expression vector in *Salmonella* cells, to obtain an efficient, stable and antigen-presenting cells intracellularly regulated secretory expression of different antigen structural domains in attenuated *Salmonella* cells.

4. A method of preparing the coronavirus vaccine based on secretory expression of attenuated *Salmonella* according to claim 1, comprising a combination of selected coronavirus antigenic epitope structural domains that can induce an optimal immune response.

5. The method of preparing the coronavirus vaccine based on secretory expression of attenuated *Salmonella* according to claim 4, wherein the combination of coronavirus antigenic epitope structural domains that can induce an optimal immune response is the SARS-CoV-2 spike protein (S protein) RBD structural domain located at positions 319-541 of full amino acid sequence of the S protein, and the RBD structural domain has a gene sequence of the nucleotide sequence shown in SEQ ID No. 6; or the combination of coronavirus antigenic epitope structural domains that can induce an optimal immune response is the SARS-CoV-2 spike protein (S protein) NTD structural domain located at positions 13-303 of the full amino acid sequence of the S protein, and the NTD structural domain of the ARS-CoV-2 spike protein has a gene sequence of the nucleotide sequence shown in SEQ ID No. 7; or the combination of coronavirus antigenic epitope structural domains that can induce an optimal immune response is part of the sequence of the SARS-CoV-2 spike protein (S protein) S2 structural domain located at positions 886-1077 of the full amino acid sequence of the S protein, and the S2 structural domain has a gene sequence of the nucleotide sequence shown in SEQ ID No. 8.

6. The method of preparing the coronavirus vaccine based on secretory expression of attenuated *Salmonella* according to claim 4, wherein the intracellular inducible promoter in the antigen presenting cells is *Salmonella* SifB promoter having a gene sequence of the nucleotide sequence shown in SEQ ID No. 4; the plasmid anti-loss element is AT element sequence having a gene sequence of the nucleotide sequence shown in SEQ ID No. 10; the secretory expression system containing bacterial secretion signal is the *Salmonella* type III secretory expression system, the *Salmonella* type III secretion signal is *Salmonella* virulence island 2 (SPI-2) effector protein SseJ signal peptide having a gene sequence of the nucleotide sequence shown in SEQ ID No. 5; expression of multiple vaccine antigens is achieved by attenuated *Salmonella*, and the attenuated *Salmonella* is VNP20009 or htrA gene-deficient attenuated *Salmonella* VNP20009 (Ah-1).

7. A method of preparing the coronavirus vaccine based on secretory expression of attenuated *Salmonella* according to claim 1, comprising the steps of: preparing a vaccine of a strain mixture of multiple recombinant attenuated *Salmonella*, the strain mixture comprises two recombinant attenuated *Salmonella* strains loaded with Ah-BJ-RBD and Ah-BJ-NTD expression plasmids, respectively, and the strain mixture comprises at least two of the abovementioned strains.

8. The SARS-CoV-2 coronavirus vaccine based on secretory expression of attenuated *Salmonella* according to claim 1, wherein the vaccine further comprises a recombinant VNP20009 (Ah-1) strain that expresses a SARS-CoV-2 spike protein (S protein) NTD structural domain located at positions 13-303 of the full amino acid sequence of the S protein, and the NTD structural domain of the ARS-CoV-2 spike protein has a gene sequence of the nucleotide sequence shown in SEQ ID No. 7.

9. The SARS-CoV-2 coronavirus vaccine based on secretory expression of attenuated *Salmonella* according to claim 1, wherein the vaccine further comprises a recombinant VNP20009 (Ah-1) strain that expresses part of the sequence of the SARS-CoV-2 spike protein (S protein) S2 structural domain located at positions 886-1077 of the full amino acid sequence of the S protein shown in SEQ ID No. 8.

10. A SARS-CoV-2 coronavirus preventive drug comprising the SARS-CoV-2 coronavirus vaccine according claim 1.

* * * * *